US006156533A

United States Patent [19]
Oriel et al.

[11] Patent Number: 6,156,533
[45] Date of Patent: Dec. 5, 2000

[54] METHOD FOR DEGRADATION OF PINENES BY BACILLUS ISOLATES

[75] Inventors: Patrick J. Oriel, Midland; Natarajan S. Savithiry, Okemos; Weijie Fu, Madison Heights, all of Mich.

[73] Assignee: Board of Trustees Operating Michigan State University, East Lansing, Mich.

[21] Appl. No.: 09/079,335

[22] Filed: May 14, 1998

Related U.S. Application Data

[60] Provisional application No. 60/046,742, May 16, 1997.

[51] Int. Cl.[7] .................................. C12P 7/02; C12P 7/00; C12P 7/24; C12P 1/00; C12N 1/20
[52] U.S. Cl. .......................... 435/41; 435/132; 435/147; 435/252.5; 435/155; 435/148
[58] Field of Search .................. 435/252.5, 132, 435/147, 155, 41, 148

[56] References Cited

U.S. PATENT DOCUMENTS

| | | |
|---|---|---|
| 4,495,284 | 1/1985 | Rhodes et al. . |
| 5,487,988 | 1/1996 | Chang et al. . |
| 5,652,137 | 7/1997 | Chang et al. ................. 435/252.5 |

OTHER PUBLICATIONS

Sambrook, et al., Molecular Cloning: A Laboratory Manual, 2nd Ed., Cold Spring Harbor Laboratory, Cold Spring Harbor, New York (1989) (Appendix A).
Chang and Oriel, J. Food Sci. vol. 59:660–662 (1994).
Chang, et al., J. Food Science vol. 60:551–553 (1995).

*Primary Examiner*—Ponnathapu Achutamurthy
*Assistant Examiner*—Peter P. Tung
*Attorney, Agent, or Firm*—Ian C. McLeod

[57] ABSTRACT

A novel isolate of Bacillus isolated from white pine is described. The isolate is used to produce monoterpene derivatives. Also described is a pinene hydroxylase enzyme from the isolate. The enzyme is a general allylic oxidizer.

12 Claims, 6 Drawing Sheets

METHOD FOR DEGRADATION OF PINENES BY BACILLUS ISOLATES

This application is based upon Provisional Application Ser. No. 60/046,742 filed May 16, 1997.

BACKGROUND OF THE INVENTION

(1) Summary of the Invention

The present invention relates to aerobic thermophiles which have the ability to use the monoterpenes, α- and β-pinene, limonene, carveol, and carvone as sole carbon sources. The present invention also relates to the production of limonene, β-pinene, α-terpineol, carvone, and carveol from monoterpene substrates using the aerobic thermophile isolate BR425. The present invention further relates to an isolated pinene hydroxylase that is a general allylic oxidizer.

(2) Description of Related Art

Pinenes, the major constituents of turpentine, are bicyclic monoterpenes which are produced in significant quantities by plants of the Pinaceae family. Because of their volitility, pinene emissions from conifer forests and during pulping operations constitute a major source of biogenic hydrocarbons (Lindskag and Potter, Chemosphere (1992), Vol. 30, pp. 1171–181; Stromvall and Petersson, Environ. Pollution (1993), Vol. 79, pp.219–223). Pinenes are useful for manufacture of a wide variety of consumer products. α-pinene is used to manufacture pine oil which is used in disinfectants, detergents mining chemicals, insecticides and resins. β-pinene is a valuable raw material used in the manufacture of cosmetic fragrances and culinary flavorings. Pinenes are the major constituents of turpentine oils and consequently are very cheap to obtain and are readily available. Pinenes can be converted to several higher value monoterpenes such as carvone, α-terpineol and limonene which is usually performed by a series of complex synthetic chemical reactions (Kirk-Othmer, *Encyclopedia of Chemical Technology*, $3^{rd}$ Edition., Vol. 22. (1983), Mark et al. Eds. John Wiley & Sons. New York, N.Y. pp. 709–749). Limonene is also a substrate for synthetic chemical production of monoterpenes such as carvone, perillyl alcohol and α-terpineol. It has been recognized that producing higher value monoterpenes from pinenes could be simplified if these compounds could be produced by microbial means.

U.S. Pat. No. 4,495,284 to Rhodes and Winskill describes the preparation of 1-carvone (spearmint flavor) by cultivating Pseudomonas strain NCIB 11671 in an aqueous nutrient media in the presence of 1-α- or 1-β-pinene. However, Pseudomonas is not thermophilic and therefore cannot be cultivated under conditions favoring monoterpene volatilization which can be advantageous in bioprocessing applications. Furthermore, the strain was not disclosed as being capable of degrading other monoterpene substrates.

U.S. Pat. No. 5,487,988 to Chang and Oriel describes a process for the preparation of monoterpene compounds such as perillyl alcohol, perillyl aldehyde, and α-terpineol from limonene using thermophilic *Bacillus stearothermophilus* strain BR388. The Bacillus was not disclosed as being capable of degrading other monoterpene substrates such as pinenes.

While the above-mentioned U.S. Patent to Rhodes and Winskill discloses a strain of Pseudomonas capable of degrading pinenes and disclose use of the microorganism for producing 1-carvone from pinenes, the metabolism of pinenes by microorganisms has been little studied, since pinenes are both poorly soluble in aqueous media and membrane destructive, and therefore toxic to procaryotic and eucaryotic microorganisms (Andrews et al., Appl. Environ. Microbiol.(1980), Vol. 40, pp. 301–304).

In early reports, catabolism of α-pinene by Pseudomonas strain PL was suggested to proceed either by isomerization of the pinene to limonene with subsequent oxidation to perillic acid (Shukla and Bhattacharyya, Ind. J. Biochem. (1968), Vol. 5, pp 92–99) or by direct oxidation to pinene epoxide prior to ring cleavage (reviewed by Tudgill, Biodegradation, (1990), Vol. 1, pp. 93–1005). Recent evidence indicates the presence of a second silent pathway in one of the pinene-epoxidizing Pseudomonas strains, the metabolites for which have not been identified (Colocousi et al., Appl. Microbiol. Biotechnol. (1996), Vol. 45, pp. 822–830). To date none of the genes involved in the pinene catabolic pathway have been examined.

Thermophilic microorganisms have not been described that are capable of degrading pinenes at elevated temperatures which would allow production of higher value monoterpenes under conditions favoring monoterpene volatilization.

DESCRIPTION OF PREFERRED EMBODIMENTS

The present invention relates to a process for the preparation of derivatives of a monoterpene which comprises providing a culture medium containing cells of an isolated thermophilic microorganism in pine sap encoding pinene hydroxylase and not pinene oxide lyase activity and which can use pinene as a sole carbon source and incubating the cells in the culture medium in the presence of the monoterpene to produce an isolatable amount of the monoterpene derivatives.

The present invention further relates to a process for producing high value monoterpene derivatives which comprises providing a culture medium containing cells of an isolated thermophilic microorganism in pine sap encoding pinene hydroxylase and not pinene oxide lyase activity and which can use pinene as a sole carbon source and incubating the cells in the culture medium in the presence of a low value monoterpene to produce an isolatable amount of the high value monoterpene derivative.

The monoterpenes to be derivatized are selected from the group consisting of α-pinene, β-pinene, limonene, carveol, and carvone. The monoterpene derivatives are selected from the group consisting of limonene, β-pinene, carveol, carvone and α-terpineol. Low value monoterpenes are selected from the group consisting of, in order of increasing value, α-pinene, limonene and carveol. High value monoterpene derivatives are selected from the group consisting of limonene, β-pinene, α-terpineol and carvone. The monoterpenes derivatized and the monoterpene substrates are all members of the group consisting of monoterpenes.

Another embodiment of the present invention relates to a process for producing limonene from α-pinene which comprises providing a culture medium containing cells of an isolated thermophilic microorganism in pine sap encoding pinene hydroxylase and not pinene oxide lyase activity and which can use pinene as a sole carbon source; and incubating the cells in the culture medium in the presence of the α-pinene to produce an isolatable amount of limonene.

Another embodiment of the present invention relates to a process for producing a mixture of limonene, carveol and carvone from a pinene which comprises providing a culture medium containing cells of an isolated thermophilic microorganism in pine sap encoding pinene hydroxylase and not pinene oxide lyase activity and which can use pinene as a sole carbon source; and incubating the cells in the culture medium in the presence of the pinene to produce an isolatable amount of the mixture of limonene, carveol and carvone.

A still further embodiment of the present invention relates to a process for producing α-terpineol, carveol and carvone from limonene which comprises providing a culture medium containing cells of an isolated thermophilic microorganism in pine sap encoding pinene hydroxylase and not pinene oxide lyase activity and which can use pinene as a sole carbon source; and incubating the cells in the culture medium in the presence of the limonene to produce an isolatable amount of the mixture of α-terpineol, carveol and carvone.

Another embodiment of the present invention relates to a process for producing β-pinene from α-pinene which comprises providing a culture medium containing cells of an isolated thermophilic microorganism in pine sap encoding pinene hydroxylase and not pinene oxide lyase activity and which can use pinene as a sole carbon source; and incubating the cells in the culture medium in the presence of the α-pinene to produce an isolatable amount of the β-pinene.

In all of the aforementioned embodiments, the monoterpene is provided to the culture medium as a vapor. The monoterpene can also be added in increments over time directly to the culture medium. The monoterpene can also be provided to the culture as a separate phase, the second phase also used to extract the monoterpene derivatives. The incubation temperature to produce the monoterpene derivative from the monoterpene substrate is at a temperature between 45° C. and 60° C., preferably at a temperature of 50° C.

This invention relates to degradation of (R)-α- and (S)-β-pinene and other monoterpenes by the isolated thermophilic microorganism which is a member of the Bacillus family and preferably isolates BR424 and BR425 which were isolated from a trunk wound exudate from a white pine in Michigan. The Bacillus isolate BR425 was deposited under the terms of the Budapest Treaty at the American Type Culture Collection (ATCC) 10801 University Blvd., Manassas, Va. 20110-2209 on May 7, 1997 as ATCC 55970. The Bacillus isolate BR424 was deposited under the terms of the Budapest Treaty as PTA-759 on Sep. 3, 1999

The present invention also relates to an isolated pinene hydroxylase enzyme produced by Bacillus isolate 424. The pinene hydroxylase is a general allylic oxidizer.

The present invention also relates to the preparation of derivatives of a monoterpene which comprises mixing the isolated pinene hydroxylase with the monoterpene and isolating the monoterpene derivatives. The hydroxylase may also be provided as a crude cell extract containing the pinene hydroxylase.

The present invention further relates to an isolated DNA encoding the pinene hydroxylase. The isolated DNA can be used to produce the hydroxylase in vitro or cloned into another organism that does not normally produce the hydroxylase to produce the hydroxylase. The isolated DNA may also contain an operon encoding the several genes involved in the pinene degradation pathway to produce the enzymes in vitro or cloned into another organism to produce the enzymes. The enzymes produced in vitro or by the organism are used to prepare derivatives of monoterpenes which comprises mixing the enzymes or organism with a monoterpene to produce an isolatable amount of the monoterpene derivative. It is also envisioned that various combinations of genes from the operon could be used that would produce in vitro or when cloned into another organism a combination of enzymes to produce a specific monoterpene derivative from a monoterpene substrate. For example, the genes encoding the enzymes that convert α-pinene to limonene and the enzyme that converts limonene to α-terpineol are cloned into an organism or used in vitro to exclusively produce α-terpineol from α-pinene to the exclusion of all other constituents of the degradation pathway.

Bacillus isolate BR425 is unique in that it is capable of using any one of the monoterpenes, α-pinene, β-pinene, limonene, carveol, carvone, and pinocarveol as the sole carbon source. Therefore, isolate BR425 can be used to produce a wide variety of monoterpene derivatives depending on the monoterpene carbon source provided. Previously disclosed microorganisms for producing monoterpenes have been limited to producing a single monoterpene derivative and can utilize only a single monoterpene carbon source. For example, Pseudomonas strain NCIB 11671 to produce 1-carvone from α- or β-pinenes (U.S. Pat. No. 4,495,284 to Rhodes and Winskill), *Bacillus stearothermophilus* strain BR388 to produce α-terpineol, perillyl alcohol, and aldehyde from limonene (U.S. Pat. No. 5,487,988 to Chang and Oriel), and Pseudomonas strain PL to produce perillic acid from α-pinene(Shukla and Bhattacharyya, Ibid.). Furthermore, Bacillus isolates BR424 and BR425 do not possess pinene oxide lyase activity as has been shown for Nocardia sp. (Griffiths et al., J. Bacteriol. (1987), Vol. 169, pp. 4972–4979).

The isolated pinene hydroxylase is unique in that in contrast to other monoxygenases, the enzyme uses electron acceptors rather than electron donors as a cofactor. The pinene hydroxylase uses Flavin Adenine Dinucleotide (FAD) and potassium ferricyanide as cofactors instead of the expected electron donor cofactors NADPH and NADH alone. They could be used in combination with FAD and ferricyanide. Furthermore, the pinene hydroxylase is insensitive to decreased oxygen levels and performs with equivalent efficiently under either oxygenated or anoxic conditions. The pinene hydroxylase appears to be a general allylic oxidizer.

The invention can be performed in bioreactors under conditions that favor volatilization of the monoterpene substrates and the monoterpene derivatives which can be advantageous in bioprocessing operations.

The invention will be further illustrated by means of the following examples.

EXAMPLE I

The isolation and identification of Bacillus thermophiles capable of degrading monoterpenes is described.
Reagents and Media:

The (R) enantiomer α-pinene and the (S) isomer of β-pinene were selected for microbial degradation studies as these enantiomers predominate in North American pines, and are referred to as α- and β-pinene respectively. Monoterpenes were purchased from Aldrich Company (Milwaukee, Wis.) and filter sterilized prior to use. M9 minimal salts medium (Appendix A of Sambrook et al., *Molecular Cloning: A Laboratory Manual*, 2nd. Ed.(1989), Cold Spring Harbor Laboratory, Cold Spring Harbor, N.Y.) contained (per liter)$Na_2PO_4$, 6g; $KH_2PO_4$, 3g; NaCl, 0.5g; $NH_4Cl$, pH 7.4. After autoclaving and cooling, 2 ml of 1M $MgSO_4$ and 0.1 ml of 1M $CaCl_2$ were added. LB medium was prepared as described in Appendix A of Sambrook et al., (ibid.).
Organism Isolation and Growth:

Pinene-degrading thermophiles were isolated from samples of dried wound exudate from a stand of virgin White Pine trees near Midland, Mich. They are available from the inventors at Michigan State University, East Lansing, Mich. Furthermore, isolate BR425 is available from the ATCC as 55970. Enrichments were carried out in a 125 ml bottle containing 50 ml M9 minimal salts containing 2 ml α-pinene shaken at 60° C. After 72 hours incubation, samples of the enrichment culture were diluted and grown at 60° C. on M9 salt plates in Petri dishes containing α-pinene in small glass tubes attached to the cover at 60° C. Isolates were repeatedly transferred on these plates and retained as putative pinene utilizers. One isolate, designated BR425, exhibited vigorous pinene-dependent growth, and was chosen for further study. A second isolate, designated BR424, was also evaluated.

Isolates BR424 and BR425 were plated from an enrichment culture of white pine sap exudate and demonstrated good growth at 50° C. on M9 plates with either α- or β-pinene vapor. The isolates produced small, creamy colonies in two days. Microscopic examination indicated the colonies consisted of large linear rod-shaped bacteria with terminal endospores.
16S Ribosomal RNA Sequence Analysis:

Partial analysis of the BR425 16S ribosomal RNA gene sequence was obtained using chromosomal DNA prepared as described in Chapter 9 of Sambrook et al. (ibid.). PCR amplification and sequencing of the 16S ribosomal gene was carried out as described by Maltseva et al. (Microbiology (1996), Vol. 141, pp. 1115–1122), using the Michigan State University Automated Sequencing Facility, East Lansing, Mich. Sequences were analyzed using the ribosomal database which was accessed using the GCG Program of the Michigan State University Biochemistry Department. Analysis of the 16S ribosomal gene sequence data consisted of 400 nucleotides from either end which yielded 99.1% identity to the 16S ribosomal gene of *Bacillus pallidus* (SEQ ID NO.:1) on the 5' end and 99.1% identity to the same gene on the 3' end.

On the basis of morphology, growth characteristics and partial 16S ribosomal RNA gene sequence, the thermophilic isolate BR425 may be a strain of *Bacillus pallidus*. *Bacillus pallidus* was first described by Scholz et al., (1987), Systematic and Applied Microbiol., Vol. 9, pp. 91–96) as a dominant member of yeast factory sewage and in municipal sludge. To our knowledge, this thermophile has not been a previous subject of examination for any catabolic pathway.

Figure 1:
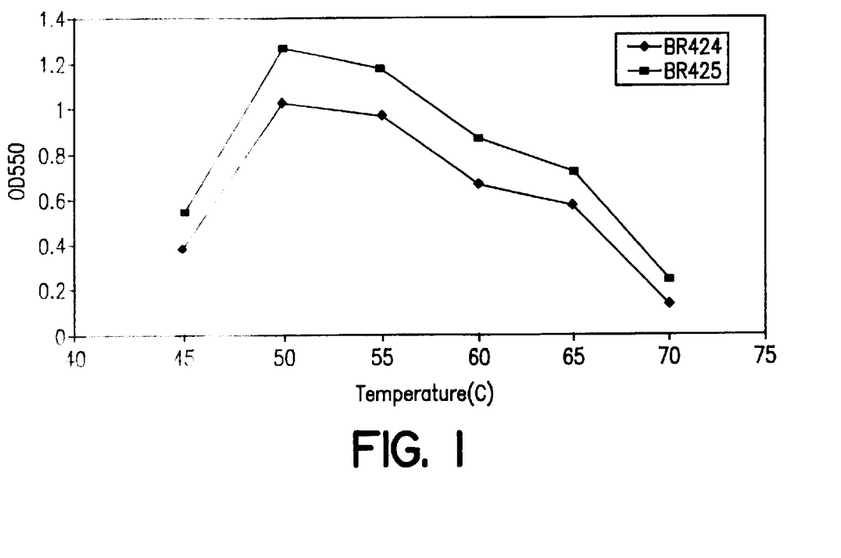
FIG. 1 is a graph showing the optimum growth temperature for Bacillus isolates BR424 and BR425. Optimal growth temperature is 50° C.

The optimal growth temperature was determined by inoculating liquid LB cultures with either isolate and incubating each culture at a temperature between the range of 45° C. and 70° C. FIG. 1 shows the thermophilic characteristics of the isolates. Both isolates were able to grow within the temperature range of 45° C. and 65° C., with optimal growth for both isolates at 50° C.

EXAMPLE II

For examination of growth rates on various substrates and metabolite production, BR425 was grown in 100 ml serum bottles containing 40 ml M9 salts and various concentrations of either α-pinene, β-pinene, limonene, carveol, carvone, or pinocarveol as the carbon source. The bottles were sealed with TEFLON-coated stoppers and aluminum caps (TEFLON is a trademark owned by E. I. du Pont and Nemours, Wilmington, Del.). Then the bottles were incubated in a water bath gyrorotatory shaker at 50° C. Growth of BR425 was assayed after incubations of 24, 48, and 72 hours as number of colony forming units (CFU).

In previous studies with *Bacillus stearothermophilus* isolates grown in media containing limonene (Chang and Oriel, J. Food Sci.(1994), Vol. 59, pp. 660–662), it was found that growth was supported without inhibition between a limited concentration range of the limonene. Growth of the present isolates were also restricted to a limited concentration range of monoterpenes.

Figure 2:
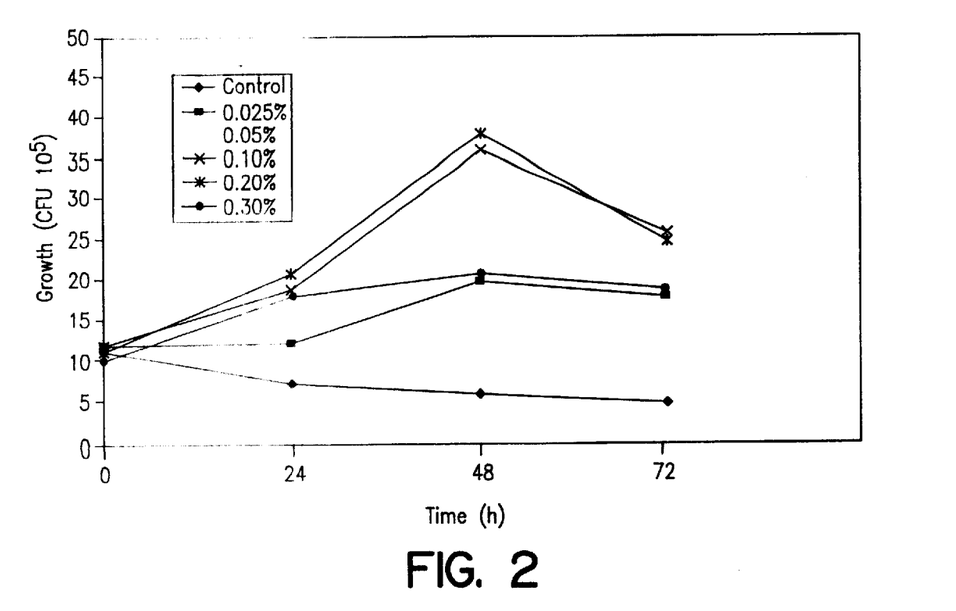
FIG. 2 is a graph showing growth of Bacillus isolate BR425 in media containing different concentrations of α-pinene. The optimal concentration of α-pinene for growth is 0.2%.
Figure 3:
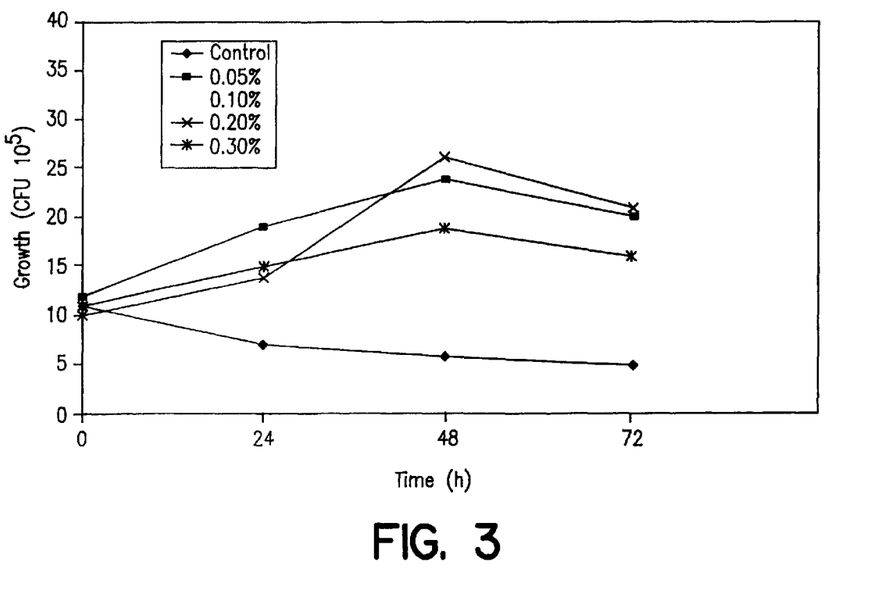
FIG. 3 is a graph showing growth of Bacillus isolate BR425 in media containing different concentrations of β-pinene. The optimal concentration of β-pinene for growth is 0.2%.
Figure 4:
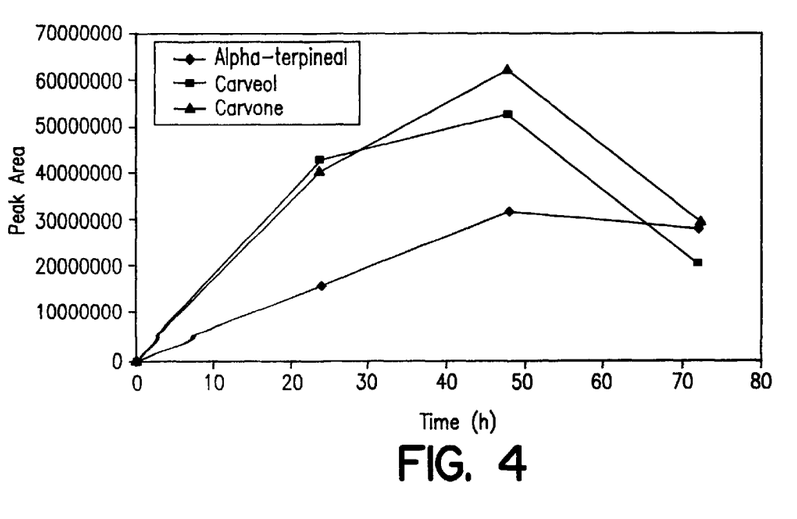
FIG. 4 is a graph showing growth of Bacillus isolate BR425 in media containing limonene to produce the bioconversion products carveol, α-terpineol, and carvone.
Figure 5:
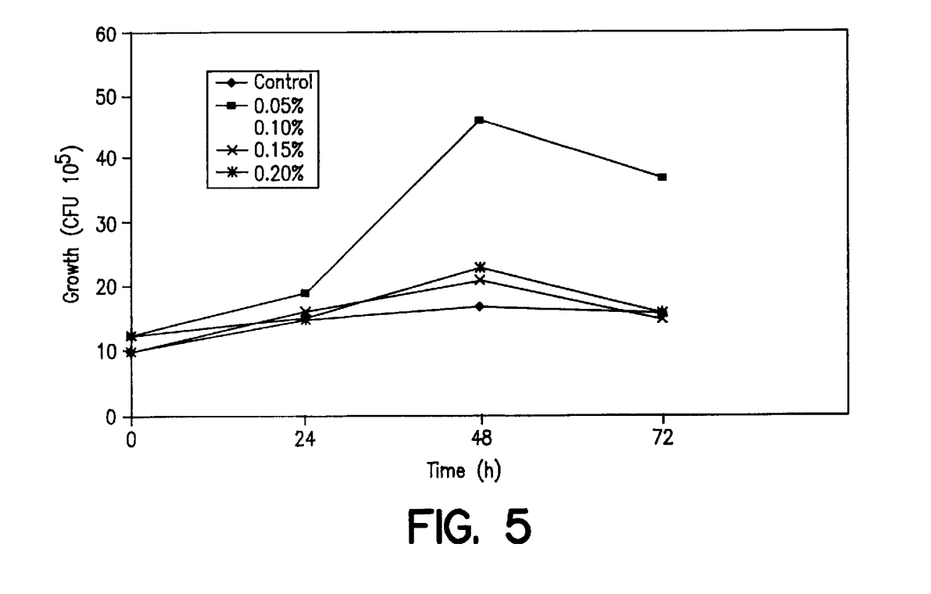
FIG. 5 is a graph showing growth of Bacillus isolate BR425 in media containing carveol at various concentrations. The optimal concentration of carveol for growth is 0.05%.
Figure 6:
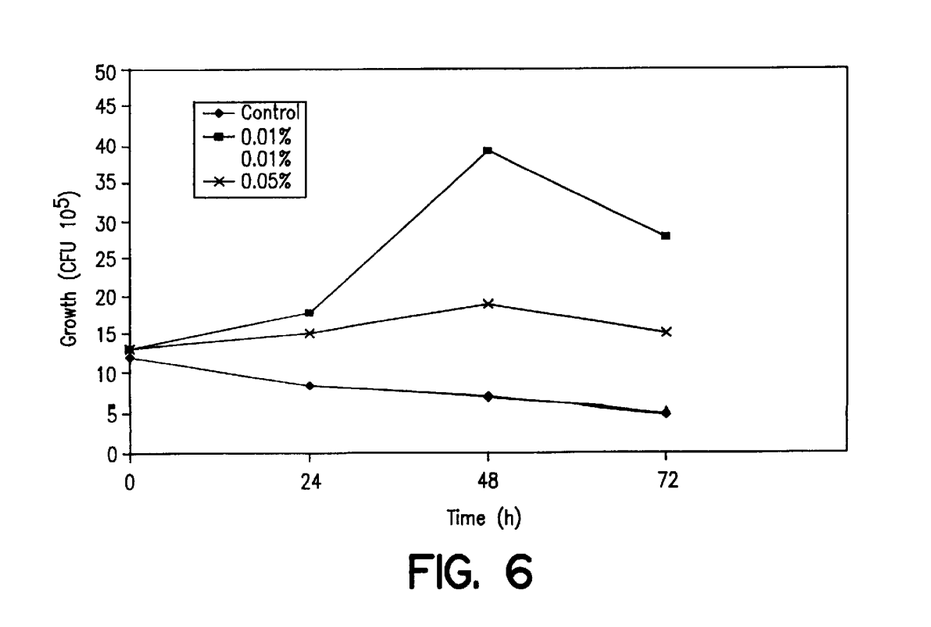
FIG. 6 is a graph showing growth of Bacillus BR425 on media containing carvone at various concentrations. The optimal concentration of carvone for growth is 0.01%.
Figure 7:
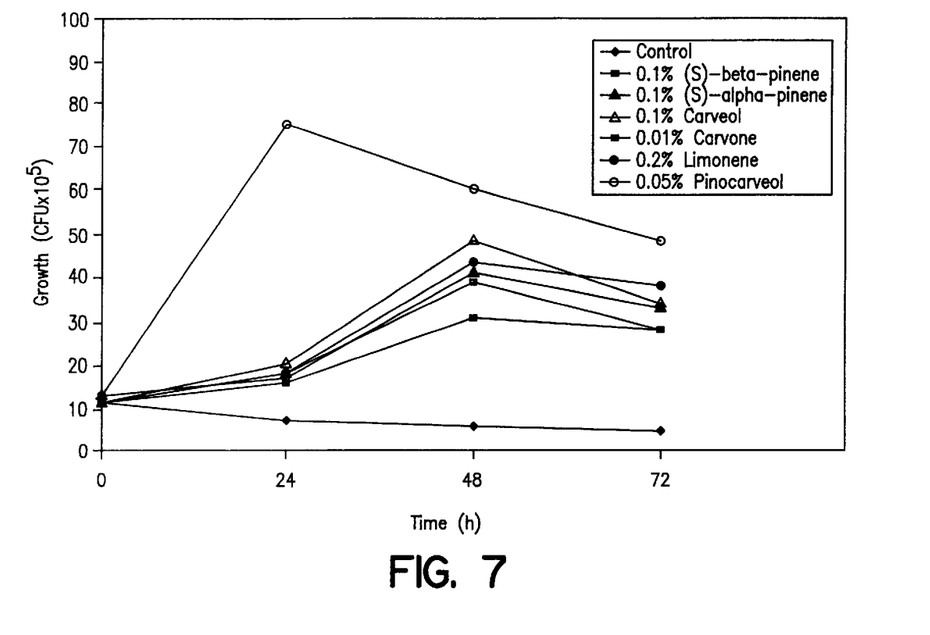
FIG. 7 shows growth of BR425 in media containing either (S) beta-pinene,. (s) alpha-pinene, limonene, carveol, carvone and pinocarveol. Symbols: Δ, No monoterpene; ○, 0.1% (S)-β-pinene; ▲, 0.1% (S)-α-pinene; ¤, 0.1% (S)-carveol; ◯, 0.01% (S)-carvone; ■, 0.2% (R)-limonene.

For Bacillus isolate BR425 incubated with α-pinene, a limited concentration range between 0.025% and 0.03% was able to support growth (FIG. 2), with optimal growth at a concentration of 0.2%. The isolate was also shown to grow in media containing any of the following related monoterpenes as the carbon source: β-pinene, carveol, carvone, and limonene. FIG. 3 shows that BR425 grew in media containing β-pinene within the concentration range of 0.05% and 0.3% with optimal growth at a concentration of 0.2%. FIG. 4 shows the production over time of α-terpineol, carveol, and carvone from cultures of BR425 grown in media containing 0.2% limonene. FIG. 5 shows that BR425 grew in media containing carveol at an optimal concentration of 0.05%, and FIG. 6 shows that BR425 grew in media containing carvone at an optimal concentration of 0.01%. FIG. 7 shows the relative growth of BR425 in media containing either 0.1% β-pinene, 0.1% α-pinene, 0.1% carveol, 0.01% carvone, 0.2% limonene, or 0.05% pinocarveol. BR425 did not appear to grow in media containing myrtenol, myrtenal, or pinene epoxide over a similar range of concentrations. While BR424 can grow on either α- or β-pinene, it did not appear to be able to grow in media containing limonene.

In contrast to *Bacillus stearothermophilus* BR388 (Chang and Oriel, ibid.) which can degrade limonene but not pinene, isolate BR425 demonstrated a fairly broad monoterpene substrate range, demonstrating growth on both (R) and (S)

α-pinene, (S)-β-pinene, (R)-limonene, carvone, and (R)-carveol. Both the BR424 and BR425 isolates proved to be subject to growth inhibition at monoterpene concentrations approaching saturation.

EXAMPLE III

For analysis of pinene biotransformation products, liquid cultures of BR425 grown to the desired time were centrifuged at 12,000 ×g for 20 minutes at 4° C., acidified to pH 2.0 with HCl and extracted three times with equal volumes each of ether. The ether fraction was evaporated to 25 ml and separated into neutral and acidic fractions by three extractions with 0.6 volumes of 5% NaOH. The ether fraction was then concentrated with nitrogen, neutralized with 5% HCl, and analyzed by Gas chromatography/mass spectrometry (GC/MS). The NaOH fraction was acidified to pH 2.0 and re-extracted three times with 0.3 volumes each of ether. Following concentration, the ether fraction was analyzed using a Hewlett-Packard HP5890 gas chromatograph with a MSD HP 5970 detector and a fused silica capillary column (0.25 mm I.D. ×30M DB-wax). Conditions used were: helium carrier gas, injection port and detector port at 240° C., column temperature from 40° C. to 240° C. at 7° C./min. with 2 min. initial hold time.

Ether extracts of BR425 culture supernatants grown in media containing α-pinene were examined after various times of culture with the results shown in Table 1. Significant amounts of neutral metabolites pinocarveol, pinocarvone, carveol and carvone were observed together with lesser amounts of myrtenol, myrtenal, limonene, and β-pinene in two independent experiments. Optimal production of pinocarveol was observed after 24 hours and optimal production of limonene, pinocarvone, carveol, and carvone was observed after 48 hours. None of these metabolites were observed in the absence of BR425. For most of these metabolites, the optimal concentration of metabolite coincided with the highest concentrations of bacteria.

Figure 9:
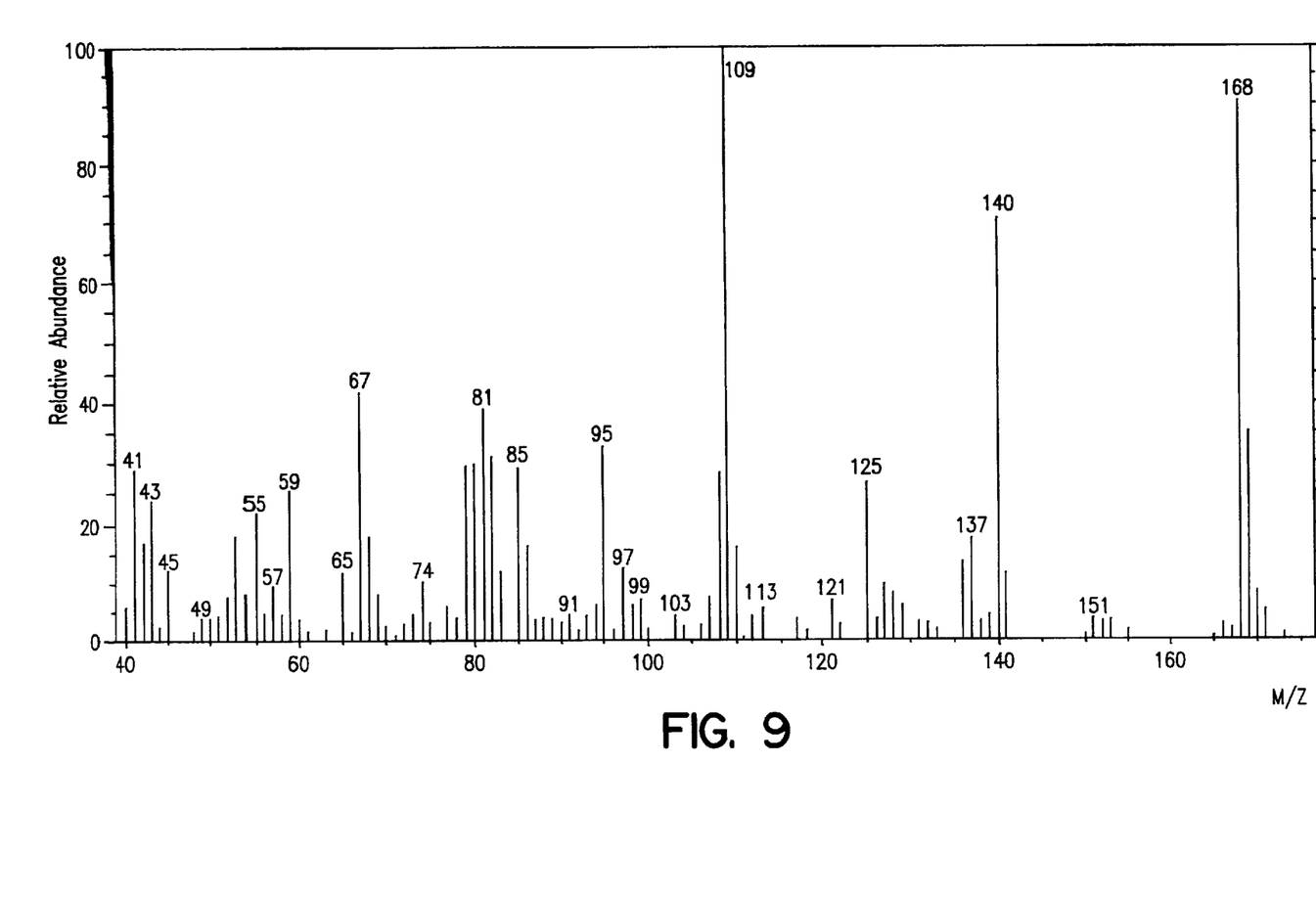
FIG. 9 is a GC/MS fragmentation pattern of the ether fraction containing pinene biotransformation products produced by Bacillus isolate BR425. Peak 168 is 2-methyl-5-isopropenyl-2,3-hexanoic acid.

In addition to these neutral monoterpene metabolites, an acid metabolite of molecular mass 168 was also observed by GS/MS analysis of ether extractions of the liquid cultures of BR425 grown in media containing α-pinene (FIG. 9). The same acid metabolite was also observed during BR425 growth on limonene.

TABLE 1

Metabolites formed during growth of Bacillus BR425 on α-pinene

| Metabolites (mg/l) | 0 hr | 24 hr | 48 hr | 72 hr |
| --- | --- | --- | --- | --- |
| β-pinene | 0 | 0.01 | 0.03 | 0.02 |
| limonene | 0 | 0.08 | 0.18 | 0.06 |
| pinocarveol | 0 | 1.02 | 0.82 | 0.52 |
| pinocarvone | 0 | 0.87 | 0.94 | 0.82 |
| myrtenol | 0 | 0.58 | 0.52 | 0.32 |
| myrtenal | 0 | 0.46 | 0.47 | 0.44 |
| carveol | 0 | 4.38 | 6.32 | 1.48 |
| carvone | 0 | 1.28 | 2.69 | 0.81 |

EXAMPLE IV

In previous work with a limonene-degrading *E. coli* recombinant, described in U.S. patent application Ser. No. 08/857,873 filed May 16, 1996 to Savithiry and Oriel and owned by a common assignee(incorporated herein by reference), it was found that incubating the recombinant *E. coli* in a two-phase bioreactor with neat limonene as the organic phase provided a convenient method for identification of neutral terpenoid metabolites, as the limonene phase insured a saturating level in the aqueous phase, while facilitating removal and concentration of the metabolites into the organic phase for direct identification using GC/MS. This same two-phase incubation method was used to access the metabolites produced by Bacillus BR425.

For the two-phase biotransformation studies of metabolites produced during incubation of BR425 cells in α- or β-pinene or limonene, 50 ml cultures of BR425 cells that had been grown in LB medium were washed with M9 medium and resuspended to a concentration of $10^9$ cells per ml in 0.1 M $K_2HPO_4$ buffer, pH 7.0. Afterwards, 0.6 ml of neat α-pinene, β-pinene, or limonene was added and the cultures were incubated with shaking in a gyrotatory water bath for 24 hours at 50° C. Samples of the monoterpene phases for each culture were directly injected into the GC/MS for analysis.

The metabolites produced during the two-phase incubations with α-pinene, β-pinene, or limonene are shown in Table 2. For cultures using α-pinene and β-pinene as substrates, metabolites similar to those identified during the growth studies in Example II were observed, except that carvone was only observed in trace quantities. With limonene as the substrate, carveol and carvone were found in significant quantities, with smaller amounts of α-terpineol.

TABLE 2

BR425 monoterpene metabolites from two-phase incubation

| Metabolites* (mg/l) | Organic Phase | | |
| --- | --- | --- | --- |
| | α-pinene | β-pinene | Limonene |
| alpha-pinene | | ND | ND |
| beta-pinene | 4.38 | | ND |
| Limonene | 1.31 | 1.1 | |
| Pinocarveol | 20.5 | 19.3 | ND |
| Pinocarvone | 7.2 | 6.8 | ND |
| Myrtenol | 23.4 | 17.1 | ND |
| Myrtenal | 19.5 | 12.5 | ND |
| alpha-terpineol | ND | ND | 1.4 |
| Carveol | 14.3 | 9.6 | 10.2 |
| Carvone | Tr | Tr | 7.5 |

*Average of two experiments at 24 h incubation.
ND: Not-detected
Tr: Trace

EXAMPLE V

Crude cell extracts were assayed for pinene oxide lyase activity. For assay of pinene oxide lyase, cells were grown in LB broth into late exponential phase. Then the cells were disrupted using brief bursts of sonification at 4° C. followed by removal of cell debris by centrifugation for 30 minutes at 15,000 ×g. The lyase activity was measured according to the spectrophotometric procedure used to measure the lyase activity of Nocardia sp. strain P18.3 (Griffiths et al., ibid.). The BR425 crude cell extracts did not contain any lyase activity.

EXAMPLE VI

Pinene hydroxylase activity was measured in crude cell extracts. Pinene hydroxylase activity in crude extracts was measured utilizing Bacillus BR424 cells grown in M9 media containing 0.1% glycerol and 0.2% α-pinene at 50° C. to late exponential phase. Cells were centrifuged and resuspended in 5 ml tris buffer, pH 8.0 to which 5 μl p-mercuricsulfonylfloride was added to inhibit proteases. Cells were sonicated 3 minutes in 30 second bursts with cooling, and centrifuged at 15,000 ×g for 30 minutes to provide a crude enzyme extract. The extract was assayed for pinene hydroxylase activity in a mixture consisting of 200 µl of the enzyme extract and 500 µl a solution containing 50 mM α-pinene, 1 mM FAD (Flavin Adenine Dinucleotide), 1 mM potassium ferricyanide in 50 mM tris buffer, pH 8.0. In other assays, FAD and potassium ferricyanide was replaced by NADPH and NADH. Following initial product analysis with GC/MS, carveol production was measured utilizing High Pressure Liquid Chromatography (HPLC) using 60% acetonitrile and 40% water and separating the carveol product from the pinene with a 3.9×150 mM Nova-Pak C18 column (Waters Corp., Milford, Mass.).

No pinene hydroxylase activity was detected in crude extracts using NADPH and NADH cofactors as required by most monooxygenases. Instead, α-pinene hydroxylase activity was detected when the electron acceptors FAD and potassium ferricyanide were supplied. As seen in Table 3, highest activity was observed utilizing a mixture of FAD and ferricyanide. Under anoxic conditions produced by nitrogen gassing prior to the reaction, no inhibition of activity was observed.

TABLE 3

Stimulation of pinene hydroxylase activity by electron acceptors.

| Additions | Enzyme activity (U/ml) |
|---|---|
| 0 | 0 |
| 0.1 mM FAD | 0.04 |
| 1 mM FAD | 0.47 |
| 1 mM FAD and 0.25 mM ferricyanide | 0.60 |
| 1 mM FAD and 0.5 mM ferricyanide | 0.94 |
| 1 mM FAD and 1.0 mM ferricyanide | 2.1 |

The pinene hydroxylase activity observed in the extracts differed from that expected for a monooxygenase, in that electron acceptors rather than electron donors functioned as cofactors.

EXAMPLE VII

The genes from Bacillus isolates BR425 and BR424 comprising the pathway encoding pinene catabolism are cloned as a contiguous DNA fragment into a DNA plasmid following the procedure disclosed in Chang et al. (J. Food Science (1995), Vol. 60, pp. 551–553. Total DNA from BR425 is isolated according to any one of the methods well known in the art. The isolated DNA is partially digested with a restriction endonuclease such as EcoRI or BamHI to generate a preponderance of DNA fragments greater than 5 kilobases (kb) which are then resolved on agarose gels. DNA fragments greater than 5 kb are isolated from the agarose gel, treated with alkaline phosphatase to remove terminal phosphates and cloned into a suitable plasmid vector cut with the same restriction endonuclease using T4 DNA ligase. Examples of suitable cloning plasmids are pBR328, the pUC series of cloning plasmids, and pUC derived cloning plasmids sold under the trademarks pBLUESCRIPT SK⁻ (owned by Stratagene, La Jolla, Calif.) and pGEM (owned by Promega Corp. Madison, Wis.). After ligation, the DNA is transformed into bacteria such as E. coli.

Bacterial transformants are spread on petri plates containing M9 salt agar medium which is then incubated with pinene vapor. Bacterial colonies that appear are transferred to additional petri plates and regrown in pinene vapor. In this manner clones containing the genes encoding pinene degradation enzymes are isolated. To ensure recovery of clones that contain all the genes encoding enzymes involved in the pinene degradation pathway, clones that grow in pinene vapor are incubated with limonene vapor. Clones positive are then incubated with carveol vapor and positive clones are then incubated with pinocarveol vapor. In this manner clones that express all the genes involved in the pinene degradation pathway are isolated.

Alternatively, a plasmid expression library is constructed from BR325 genomic DNA according to the procedure disclosed in Chapter 12 of Sambrook et al. (ibid.). The expression library is screened by incubation on petri plates containing M9 media with the appropriate monoterpene vapor as the substrate to isolate clones that express the appropriate enzyme as discussed previously.

DNA from positive clones is isolated, digested with restriction endonucleases and the DNA fragments resolved on an agarose gel. The DNA fragments are isolated from the agarose gel and the DNA sequence for each DNA fragment is determined by any of the art known methods such as those disclosed in Chapter 13 of Sambrook et al. (ibid.).

From the DNA sequences of the cloned DNA fragments, the pinene hydroxylase gene as well as the genes encoding the other enzymes involved in the pinene degradation pathway are identified. Each identified gene can be separately cloned into a DNA plasmid and transformed into bacteria. Alternatively, various combinations of genes, each attached to a bacterial promoter can be cloned into a plasmid and transformed into a bacteria. In this manner, transformants that utilize one or various combinations of monoterpene substrates can be constructed. Using the appropriate combination of transformants, production of specific monoterpene derivatives from a particular monoterpene substrate without production of unwanted monoterpenes and/or other degradation products as would occur using the natural microorganism.

SUMMARY

On the basis of morphology, growth characteristics and partial 16S ribosomal RNA gene sequence compared to SEQ ID NO.:1, we have tentatively identified thermophilic isolates BR424 and BR425 as members of the Bacillus family. To our knowledge, these thermophiles appear to be new and novel Bacillus isolates with the ability to degrade monoterpenes. In contrast to a previously isolated thermophile, Bacillus stearothermophilus strain BR388 which could degrade limonene but not α- or β-pinene, isolate 424 can degrade α- or β-pinene but not limonene, and isolate BR425 has a fairly broad monoterpene substrate range, degrading both (R) and (S) α-pinene, (S)-β-pinene, (R)-limonene, and (R)-carveol. Both BR424 and BR425 proved to be subject to growth inhibition at monoterpene concentrations that approached saturation.

Figure 8:
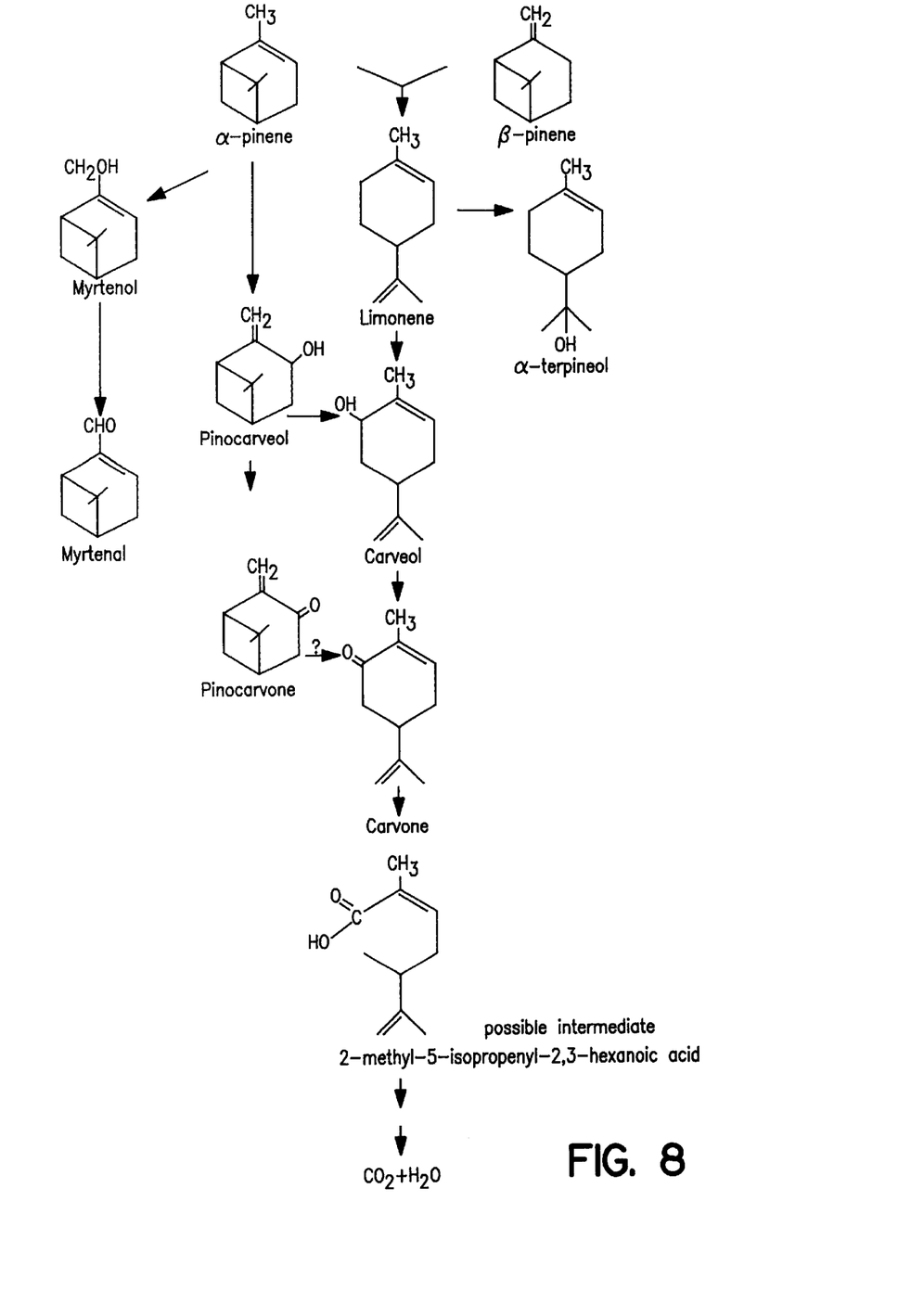
FIG. 8 is a chart showing the various pathways for pinene degradation by Bacillus isolate 425.

The appearance of limonene and carveol as degradation products of both α- and β-pinene, as well as the ability of BR425 to utilize limonene, carveol and carvone as sole carbon sources suggest that degradation of both α- and β-pinene proceeds through limonene to carveol and carvone as shown in FIG. 8. Additional utilization of pinocarveol and pinocarvone as formed as pinene metabolites cannot be excluded, however, attempts to obtain authentic samples of these intermediates were unsuccessful. Since myrtenol and myrtenal did not serve as growth substrates and since they were not depleted in later stages of growth, they appear to be dead-end metabolites. Since growth was not observed on pinene oxide and no pinene oxide lyase activity was observed in BR425 cell extracts (data not shown), utilization of a pathway utilizing pinene oxide appears unlikely. The acid metabolite observed during growth on both α-pinene and limonene adds additional evidence that BR425 catabolizes α-pinene via limonene and carveol prior to ring breakdown. The acid pinene metabolite is similar but not identical with that described for either Norcardia sp strain P18.3 (Griffiths et al., ibid.) or *Pseudomonas putida* (Tudroszen et al., Biochem. J.(1977), Vol. 168, pp. 315–318). Further work is required to definitively identify this metabolite, and elucidate further details of the pathway.

The pinene hydroxylase activity observed in crude extracts differs from that expected for a monooxygenase, in that electron acceptors rather that electron donors function as cofactors. The hydroxylase appears to be a general allylic oxidizer.

BR425 demonstrates a catabolic pathway for pinenes which utilizes carveol as a key intermediate. Carveol formation was previously reported during pinene catabolism by Pseudomonas, but was regarded as a spontaneously-formed dead-end intermediate (Gibbon and Pirt, FEBS Letts.(1971), Vol. 18, pp. 103–105; Trudgill, ibid.). Since α-pinene, β-pinene and limonene are interconvertible structural isomers (Shukla and Bhattacharyya, ibid.), it will be interesting to determine the mechanism of β-pinene and limonene formation during α-pinene catabolism, and to establish whether the pinene hydroxylase is sufficiently broad-spectrum to catalyze limonene hydroxylation.

The invention provides thermophilic microorganisms that can produce a variety of monoterpene derivatives from a variety of monoterpene substrates. The invention also provides a method for producing monoterpene derivatives from a monoterpene substrate. The invention further provides an isolated pinene hydroxylase that is a general allylic oxidizer. Finally, the invention provides an isolated DNA encoding the genes in the degradation of monoterpenes as DNA clones, which clones enable in the appropriate combination the production any one monoterpene derivative from another monoterpene substrate.

It is intended that the foregoing description be only descriptive of the present invention and that the present invention be limited only by the hereinafter appended claims.

We claim:

1. A substantially pure isolate of Bacillus designated as BR425 and deposited as ATCC 55970.

2. A substantially pure isolate of Bacillus designated as BR424 and deposited as ATCC PTA 759.

3. A substantially pure isolate of a thermophilic Bacillus, designated as BR424 and deposited as ATCC PTA 759 or designated as BR425 and deposited as ATCC 55970, with a phenotype comprising growth optimally at a temperature of 50° C., rod-shaped with terminal endospores, and capable of using as a sole carbon source a monoterpene selected from the group consisting of α-pinene and β-pinene and which is isolated from a trunk wound exudate of white pine.

4. A method for the preparation of derivatives of a monoterpene which comprises:
   (a) culturing a thermophilic Bacillus, designated as BR424 and deposited as ATCC PTA 759 or designated as BR425 and deposited as ATCC 55970, which is capable of using pinene as a sole carbon source and is isolated from a trunk wound exudate of white pine with the monoterpene in a culture medium; and
   (b) isolating the derivatives.

5. The method of claim 1 wherein the derivatives are a mixture of limonene, α-terpineol, carveol and carvone.

6. The method of claim 1 wherein the derivatives of the monoterpene are extracted from the culture medium by a solvent phase which is the solvent phase that provides the monoterpene to the medium.

7. A method for preparation of derivatives of a monoterpene which comprises:
   (a) providing a culture medium containing cells of an isolated thermophilic Bacillus, deposited as ATCC 55970 or ATCC PTA-759, expressing pinene hydroxylase and not pinene oxide lyase activity and which can use pinene as a sole carbon source and which is isolated from a trunk wound exudate of white pine;
   (b) incubating the cells in the culture medium in the presence of the monoterpene to produce an isolatable amount of the monoterpene derivatives in the culture medium; and
   (c) isolating the derivatives from the culture medium.

8. A method for preparation of high value monoterpene derivatives from low value monoterpenes which comprises:
   (a) providing a culture medium containing cells of an isolated thermophilic Bacillus, deposited as ATCC 55970 or ATCC PTA-759, expressing pinene hydroxylase and not pinene oxide lyase activity and which can use pinene as a sole carbon source and which is isolated from a trunk wound exudate of white pine;
   (b) incubating the cells in the culture medium in the presence of the low value monoterpene selected from the group consisting of α-pinene, β-pinene, limonene, or carveol to produce an isolatable amount of the high value monoterpene derivative selected from the group consisting of limonene, β-pinene, carvone, or α-terpineol in the culture medium; and
   (c) isolating the high value derivatives from the culture medium.

9. A method for producing limonene from α-pinene which comprises:

a providing a culture medium containing cells of an isolated thermophilic Bacillus, deposited as ATCC 55970 or ATCC PTA-759, expressing pinene hydroxylase and not pinene oxide lyase activity and which can use pinene as a sole carbon source and which is isolated from a trunk wound exudate of white pine;

(b) incubating the cells in the culture medium in the presence of the α-pinene to produce an isolatable amount of limonene in the culture medium; and (c) isolating the α-pinene from the culture medium.

10. A method for producing β-pinene from α-pinene which comprises:

(a) providing a culture medium containing cells of an isolated thermophilic Bacillus, deposited as ATCC 55970 or ATCC PTA-759, which can use pinene as a sole carbon source and which is isolated from a trunk wound exudate of white pine;

(b) incubating the cells in the culture medium in the presence of the α-pinene to produce an isolatable amount of the β-pinene in the culture medium; and (c) isolating the β-pinene from the the culture medium.

11. A method for producing a mixture of limonene, carveol and carvone from a pinene which comprises:

(a) providing a culture medium containing cells of an isolated thermophilic Bacillus, deposited as ATCC 55970 or ATCC PTA-759, expressing pinene hydroxylase and not pinene oxide lyase activity and which can use pinene as a sole carbon source and which is isolated from a trunk wound exudate of white pine;

(b) incubating the cells in the culture medium in the presence of the pinene to produce an isolatable amount of limonene, carveol and carvone in the culture medium; and (c) isolating the limonene, carveol and carvone from the culture medium.

12. A method for producing α-terpineol, carveol and carvone from limonene which comprises:

(a) providing a culture medium containing cells of an isolated thermophilic Bacillus, deposited as ATCC 55970 or ATCC PTA-759, expressing pinene hydroxylase and not pinene oxide lyase activity and which can use pinene as a sole carbon source and which is isolated from a trunk wound exudate of white pine;

(b) incubating the cells in the culture medium in the presence of the limonene to produce an isolatable amount of α-terpineol, carveol and carvone in the culture medium; and (c) isolating the α-terpineol, carveol and carvone from the culture medium.

* * * * *

UNITED STATES PATENT AND TRADEMARK OFFICE
CERTIFICATE OF CORRECTION

PATENT NO. : 6,156,533
DATED : December 5, 2000
INVENTOR(S) : Patrick J. Oriel, Natarajan S. Savithiry and Weije Fu It is certified that error appears in the above-identified patent and that said Letters Patent is hereby corrected as shown below:

Column 13, claim 5,
Line 60, "of Claim 1" should be -- of Claim 4 --.

Column 13, claim 6,
Line 62, "of Claim 1" should be -- of Claim 4 --.

Column 15, claim 9,
Line 1, "a providing" should be -- (a) providing --.

Signed and Sealed this

Thirtieth Day of October, 2001

Attest:

NICHOLAS P. GODICI
Attesting Officer    Acting Director of the United States Patent and Trademark Office

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 1516 base pairs
      (B) TYPE: nucleic acid
      (C) STRANDEDNESS: single
      (D) TOPOLOGY: linear    (ii) MOLECULE TYPE: GENOMIC DNA    (vi) ORIGINAL SOURCE:
      (A) ORGANISM: Bacillus
      (B) STRAIN: pallidus    (ix) FEATURE:
      (A) NAME/KEY: 16S ribosomal RNA gene    (xi) SEQUENCE DESCRIPTION: SEQ ID NO: 1:

```
CTCAGGACGA ACGCTGGCGG CGTGCCTAAT ACATGCAAGT CGAGCGGACC           50

GAAGGGAGCT TGCTCCTTTA GGTTAACGGC GGACGGGTGA GTAACACGTG          100

GGCAACCTGC CCTGCAGACT GGGATAACTT CGGGAAACCG GAGCTAATAC          150

CGGATAACAC CGAAAACCGC ATGGTTTTCG GTTGAAAGGC GGCTTTTAGC          200

TGTCACTGCA GGATGGGCCC GCGGCGCATT AGCTAGTTGG TGAGGTAACG          250

GCTCACCAAG GCGACGATGC GTAGCCGACC TGAGAGGGTG ACCGGCCACA          300

CTGGGACTGA GACACGGCCC AGACTCCTAC GGGAGGCAGC AGTAGGGAAT          350

CTTCCGCAAT GGACGAAAGT CTGACGGAGC AACGCCGCGT GAGCGAAGAA          400

GGTCTTCGGA TCGTAAAGCT CTGTTGTCAG GGAAGAACAA GTGCCGTTCG          450

AACAGGGCGG TACCTTGACG GTACCTGACG AGGAAGCCAC GGCTAACTAC          500
```

-continued

```
GTGCCAGCAG CCGCGGTAAT ACGTAGGTGG CAAGCGTTGT CCGGAATTAT          550

TGGGCGTAAA GCGCGCGCAG GCGGCTCCTT AAGTCTGATG TGAAATCTCG          600

CGGCTCAACC GCGAGCGGCC ATTGGAAACT GGGGAACTTG AGTGCAGGAG          650

AGGGGAGCGG AATTCCACGT GTAGCGGTGA AATGCGTAGA GATGTGGAGG          700

AACACCAGTG GCGAAGGCGG CTCTCTGGCC TGTAACTGAC GCTGAGGCGC          750

GAAAGCGTGG GGAGCGAACA GGATTAGATA CCCTGGTAGT CCACGCCGTA          800

AACGATGAGT GCTAAGTGTT AGAGGGTATC CACCCTTTAG TGCTGCAGCA          850

AACGCATTAA GCACTCCGCC TGGGGAGTAC GGCCGCAAGG CTGAAACTCA          900

AAGGAATTGA CGGGGACCCG CACAAGCGGT GGAGCATGTG GTTTAATTCG          950

AAGCAACGCG AAGAACCTTA CCAGGTCTTG ACATCCCCTG ACAACCCTAG         1000

AGATAGGGCG TTCCCCTTTC GGGGACAGGG TGACAGGTGG TGCATGGTTG         1050

TCGTCAGCTC GTGTCGTGAG ATGTTGGGTT AAGTCCCGCA ACGAGCGCAA         1100

CCCTTGACCT TAGTTGCCAG CATTCAGTTG GGCACTCTAA GGTGACTGCC         1150

GGCTAAAAGT CGGAGGAAGG TGGGGATGAC GTCAAATCAT CATGCCCCTT         1200

ATGACCTGGG CTACACACGT GCTACAATGG GTGGTACAAA GGGCAGCGAA         1250

ACCGCGAGGT GGAGCGAATC CCAAAAAACC ACTCTCAGTT CGGATTGCAG         1300

GCTGCAACTC GCCTGCATGA AGCCGGAATC GCTAGTAATC GCGGATCAGC         1350

ATGCCGCGGT GAATACGTTC CCGGGTCTTG TACACACCGC CCGTCACACC         1400

ACGAGAGTTT GTAACACCCG AAGTCGGTGG GGTAACCCTT ACGGGAGCCA         1450

GCCGCCGAAG GTGGGACAAA TGATTGGGGT GAAGTCGTAA CAAGGTAGCC         1500

GTATCGGAAG GTGCGG                                              1516
```